(12) United States Patent
Abou Marie et al.

(10) Patent No.: US 12,685,580 B2
(45) Date of Patent: Jul. 21, 2026

(54) ELONGATED MEDICAL NEEDLE

(71) Applicant: Boston Scientific Medical Device Limited, Galway (IE)

(72) Inventors: Rund Abou Marie, Mississauga (CA); Brock Miller, Toronto (CA); Christian Balkovec, Burlington (CA); Berna Erdemir, North York (CA)

(73) Assignee: Boston Scientific Medical Device Limited, Galway (IE)

( * ) Notice: Subject to any disclaimer, the term of this patent is extended or adjusted under 35 U.S.C. 154(b) by 643 days.

(21) Appl. No.: 18/161,594

(22) Filed: Jan. 30, 2023

(65) Prior Publication Data

US 2023/0165625 A1     Jun. 1, 2023

Related U.S. Application Data

(63) Continuation of application No. PCT/IB2021/056917, filed on Jul. 29, 2021.

(60) Provisional application No. 63/058,849, filed on Jul. 30, 2020.

(51) Int. Cl.
*A61B 18/14*     (2006.01)
*A61B 18/00*     (2006.01)

(52) U.S. Cl.
CPC .... *A61B 18/14* (2013.01); *A61B 2018/00083* (2013.01); *A61B 2018/1425* (2013.01)

(58) Field of Classification Search
CPC . A61B 18/14; A61B 18/1477; A61B 18/1492;

A61B 2018/00083; A61B 2018/00357;
A61B 2018/00363; A61B 2018/00601;
A61B 2018/1425; A61B 2018/144
See application file for complete search history.

(56)     References Cited

U.S. PATENT DOCUMENTS 6,648,839 B2 *  11/2003  Manna ............... A61B 18/1402
                                                    601/3
7,077,842 B1 *   7/2006  Cosman .............. A61B 18/148
                                                    606/41

(Continued)

FOREIGN PATENT DOCUMENTS

EP          2644145 B1    11/2015
JP          2018530360 A   10/2018
WO          2018040253 A1   3/2018

OTHER PUBLICATIONS

International Search Report for PCT Application No. PCT/IB2021/056917 mailed Nov. 1, 2021.

*Primary Examiner* — Michael F Peffley
(74) *Attorney, Agent, or Firm* — Nelson Mullins Riley & Scarborough LLP; Jason R. Kraus

(57)     ABSTRACT

An elongated medical needle includes an electrically-insulated elongated body having an outer surface extending between an electrically-insulated distal section and an electrically-insulated proximal section. An insulated electrically-conductive wire is aligned proximately along the outer surface between the electrically-insulated distal section and the electrically-insulated proximal section. An exposed electrically-conductive portion is mounted at the electrically-insulated distal section. The exposed electrically-conductive portion is electrically connected to the insulated electrically-conductive wire.

20 Claims, 11 Drawing Sheets

(56)  References Cited

U.S. PATENT DOCUMENTS

| | | | |
|---|---|---|---|
| 7,250,050 B2 * | 7/2007 | Ryan ................... | A61B 18/1492 |
| | | | 606/50 |
| 11,751,905 B2 * | 9/2023 | Howard ............. | A61B 18/1206 |
| | | | 606/41 |
| 2005/0020965 A1 * | 1/2005 | Rioux ................. | A61M 25/007 |
| | | | 606/41 |
| 2011/0118735 A1 | 5/2011 | Abou-Marie et al. | |
| 2013/0310833 A1 | 11/2013 | Brown et al. | |
| 2015/0374431 A1 | 12/2015 | Davies et al. | |
| 2018/0206910 A1 | 7/2018 | Urbanski et al. | |
| 2019/0239941 A1 | 8/2019 | Schorr et al. | |

* cited by examiner

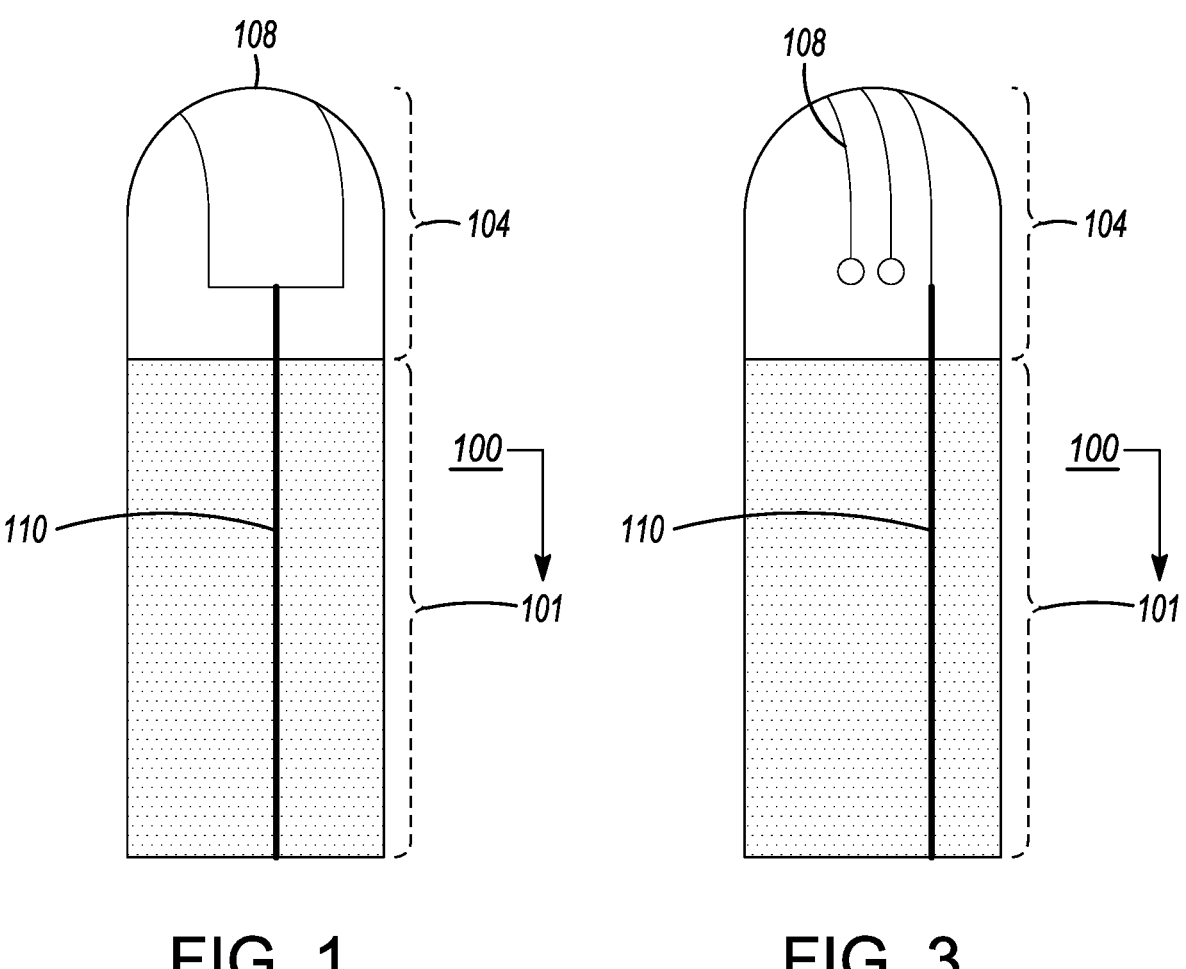
FIG. 1
FIG. 3
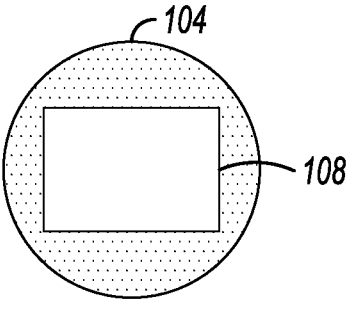
FIG. 2
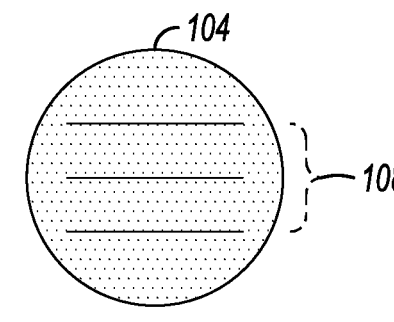
FIG. 4

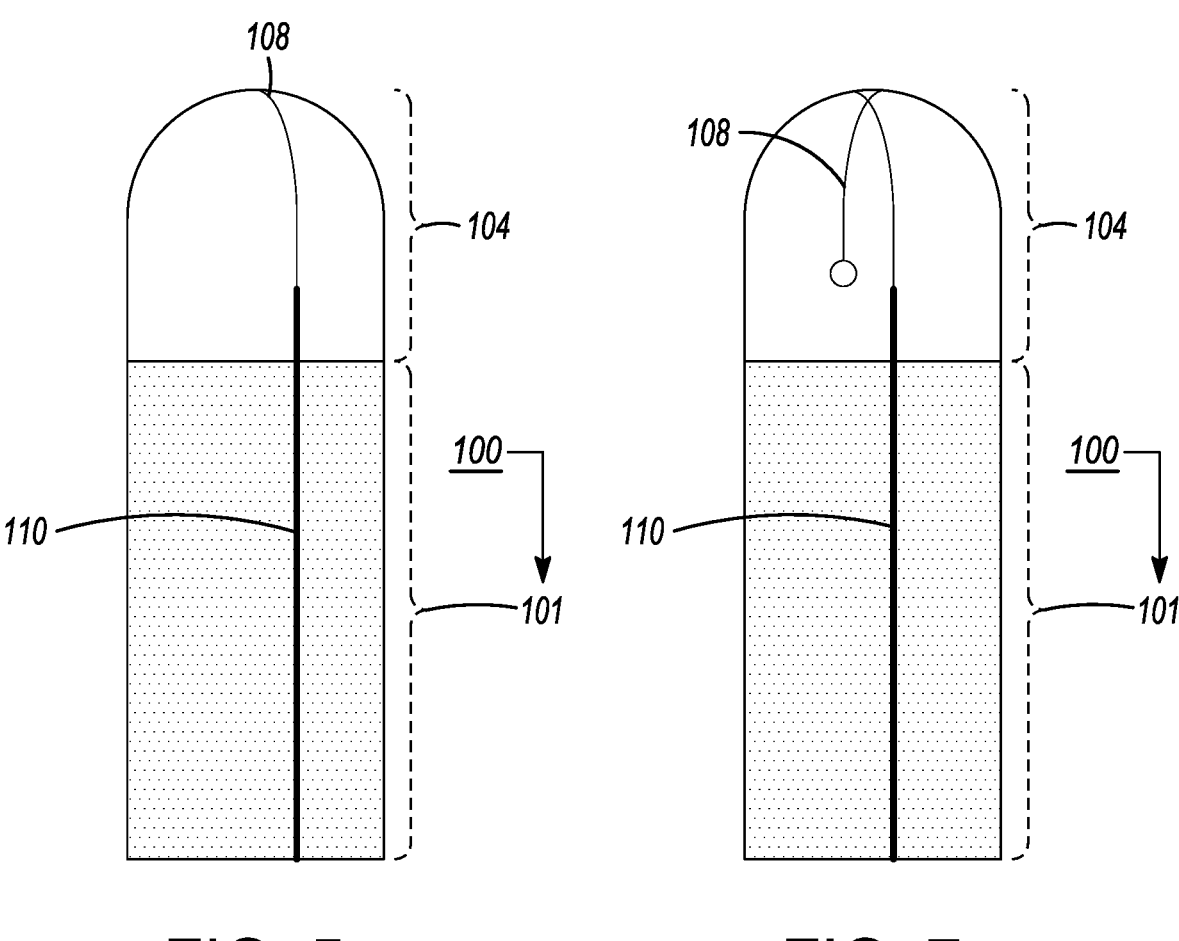
FIG. 5          FIG. 7
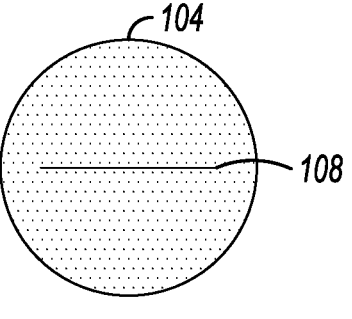
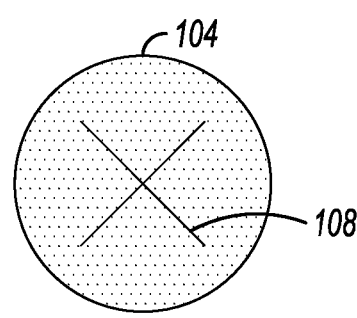
FIG. 6          FIG. 8

Section A-A

ELONGATED MEDICAL NEEDLE

CROSS REFERENCE TO RELATED APPLICATION

This application is a continuation application of International Application No. PCT/IB2021/056917, filed Jul. 29, 2021, titled "ELONGATED MEDICAL NEEDLE," which claims priority to U.S. Provisional Application No. 63/058,849, filed Jul. 30, 2020, titled "ELONGATED MEDICAL NEEDLE," the entire disclosures of which are incorporated herein by reference.

TECHNICAL FIELD

This document relates to the technical field of (and is not limited to) an elongated medical needle (and method therefor).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with existing (known) medical needle. After much study of, and experimentation with, the existing (known) medical needle, an understanding (at least in part) of the problem and its solution have been identified (at least in part) and are articulated (at least in part) as follows:

Epicardial access may be performed with a sharp mechanical needle. This needle is used to pierce the pericardium layer (of the heart) in order to gain access to the pericardial space/epicardium of the heart. This procedure may pose a high risk to the patient due to the proximity of the underlying epicardium layer and the myocardium layer beneath the thin pericardium layer. Performing this task is akin to piercing a piece of saran wrap covering a steak without damaging the steak itself.

Transseptal access of the left atrium may be performed by puncturing through the fossa ovalis from the right atrium (of the heart). A puncture device is used in conjunction with accessory devices to traverse through the femoral vein, inferior vena cava, and superior vena cava into the right atrium to be positioned in the ideal location for crossing. Using a mechanical needle to puncture through the tissue of the interatrial septum carries the risk of cardiac tamponade and is otherwise unpredictable in terms of input force required.

A radiofrequency energy-source device is configured to provide energy (such as radiofrequency energy) to a known radiofrequency medical needle for puncturing through tissue and does not require mechanical force input compared to a mechanical needle. Given this, the known radiofrequency medical needle does not need to be mechanically sharp, reducing the risk of inadvertently puncturing through the myocardium layer in the context of epicardial access, and reducing the risk of cardiac tamponade in the context of transseptal access.

The known radiofrequency medical needle may include a hollow internal lumen for facilitating injection and flow of a contrast material in addition to insertion of a guidewire. In the context of the radiofrequency medical needle, however, the internal lumen must be electrically insulated. Metal guidewires could be inserted into the lumen of the needle which may inadvertently deliver an electrical shock to (and/or burn) an operator if the inner lumen is not electrically insulated. Commonly, the body of the known radiofrequency medical needle is made of a core metal component such as stainless steel. It is able to transmit radiofrequency energy to a distal electrode for tissue puncture. Insulating the known radiofrequency medical needle from the inside may decrease the inner diameter of the needle, reducing contrast flow and potentially eliminating compatibility with a guidewire.

The known medical needle, disadvantageously, has an elongated body (the entire length of the known medical needle) that is (entirely) electrically conductive; therefore, the known medical needle may require an adequate amount of electrical insulation (for the safety of the patient and the user or operator). Providing a sufficient electrical insulation is a challenge; on the one hand, electrical insulation is required for safety; but on the other hand, utilizing an adequate amount of electrical insulation increases the overall outer diameter of the known medical needle (thereby potentially limiting the application of the known medical needle).

To mitigate, at least in part, at least one problem associated with the existing technology, there is provided (in accordance with a major aspect) an apparatus. The apparatus is for use with a biological feature of a patient. The apparatus includes and is not limited to (comprises) an elongated medical needle. The elongated medical needle is configured to be maneuvered toward, and positionable (to be positioned) proximate to, the biological feature of the patient. The elongated medical needle includes an electrically-insulated elongated body having an outer surface extending between an electrically-insulated distal section and an electrically-insulated proximal section. An insulated electrically-conductive wire is aligned proximately along the outer surface between the electrically-insulated distal section and the electrically-insulated proximal section. An exposed electrically-conductive portion is mounted at the electrically-insulated distal section. The exposed electrically-conductive portion is electrically connected to the insulated electrically-conductive wire.

To mitigate, at least in part, at least one problem associated with the existing technology, there is provided (in accordance with a major aspect) an apparatus. The apparatus is for use with a biological feature of a patient. The apparatus includes and is not limited to (comprises) an elongated medical needle. The elongated medical needle is configured to be maneuvered toward, and positionable (to be positioned) proximate to, the biological feature of the patient. The elongated medical needle includes an electrically-insulated elongated body having an outer surface extending between an electrically-insulated distal section and an electrically-insulated proximal section.

An insulated electrically-conductive wire is aligned proximately along the outer surface of the electrically-insulated elongated body. The insulated electrically-conductive wire extends between the electrically-insulated distal section and the electrically-insulated proximal section. The insulated electrically-conductive wire (located at the electrically-insulated proximal section) is configured to be electrically connectable to an energy-source device. An exposed electrically-conductive portion is mounted at the electrically-insulated distal section. The exposed electrically-conductive portion is electrically connected to the insulated electrically-conductive wire. The exposed electrically-conductive portion is configured to receive energy from the insulated electrically-conductive wire; this is done, preferably, in response to the insulated electrically-conductive wire receiving the energy from the energy-source device. The exposed electrically-conductive portion is configured to emit the energy (that was received from the insulated electrically-conductive wire) toward the biological feature after (A) the elongated medical needle was maneuvered toward, and was positioned proximate to, the biological feature, and (B) the insulated electrically-conductive wire, in use, received energy from the energy-source device.

To mitigate, at least in part, at least one problem associated with the existing technology, there is provided (in accordance with a major aspect) a method. The method is for emitting energy toward a biological feature of a patient. The method includes and is not limited to (comprises) maneuvering and positioning the elongated medical needle toward, and proximate to, the biological feature of the patient. The method also includes sending the energy to the exposed electrically-conductive portion, in use, along the insulated electrically-conductive wire in response to the insulated electrically-conductive wire receiving the energy from the energy-source device. The method also includes emitting the energy from the exposed electrically-conductive portion, in use, toward the biological feature (the energy was received from the insulated electrically-conductive wire); this is done, preferably, after (A) the elongated medical needle was maneuvered toward, and was positioned proximate to, the biological feature, and (B) the insulated electrically-conductive wire, in use, received energy from the energy-source device.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which:

FIG. 1 to FIG. 9K depict side perspective views (FIG. 1, FIG. 3, FIG. 5 and FIG. 7) and top views (FIG. 2, FIG. 4, FIG. 6, FIG. 8 and FIG. 9A to 9K) of embodiments of an elongated medical needle.

4

Figure 18A:
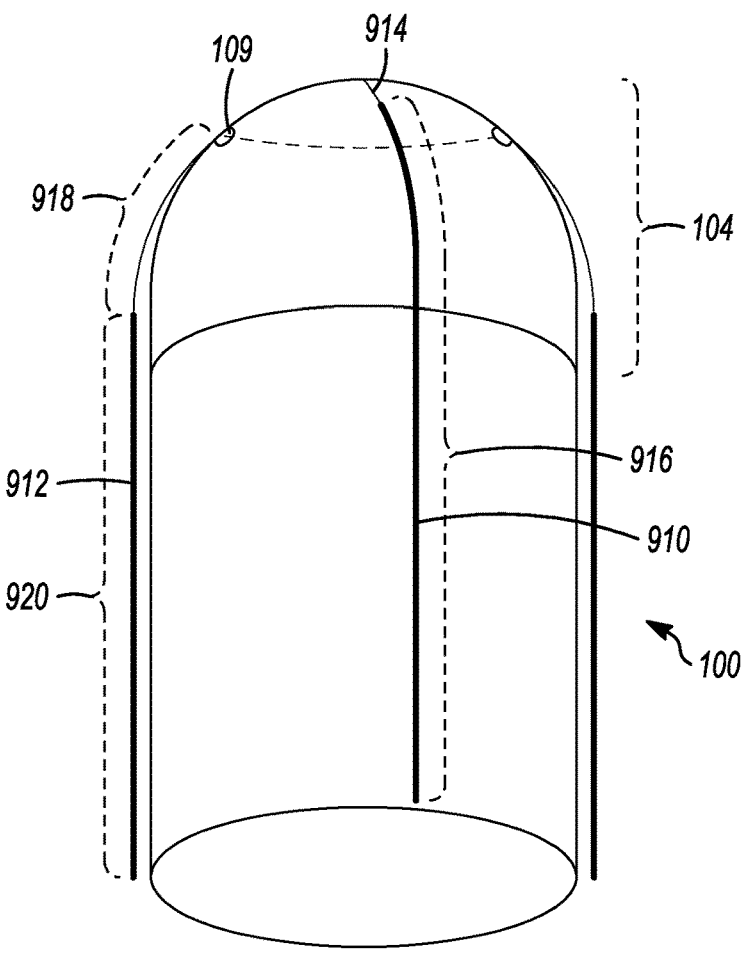
Figure 18B:
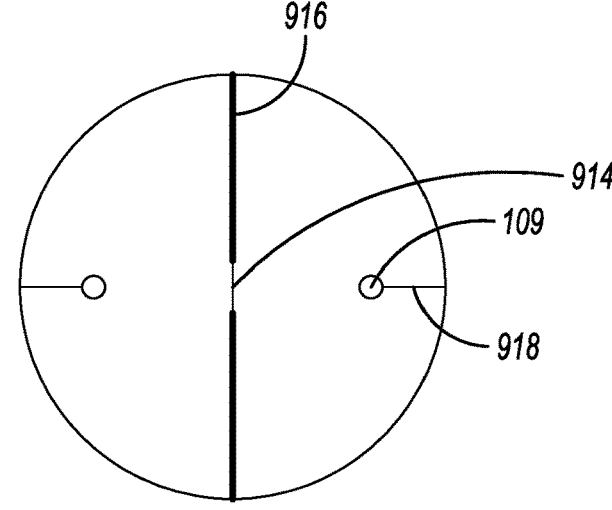
Figure 19A:
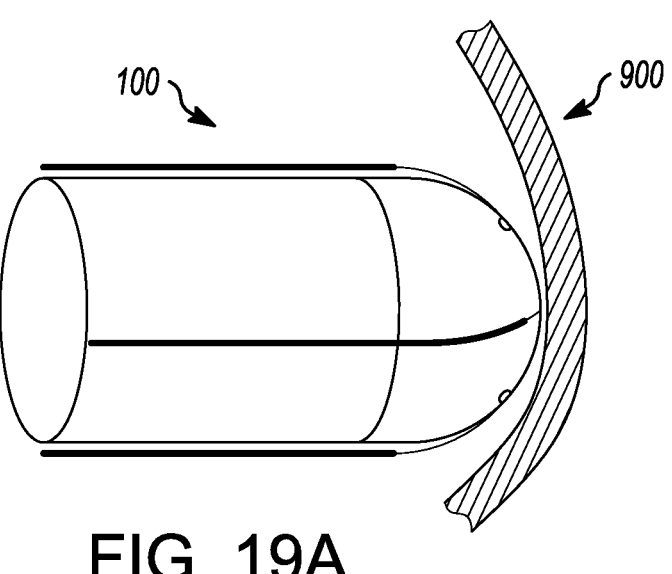
Figure 19B:
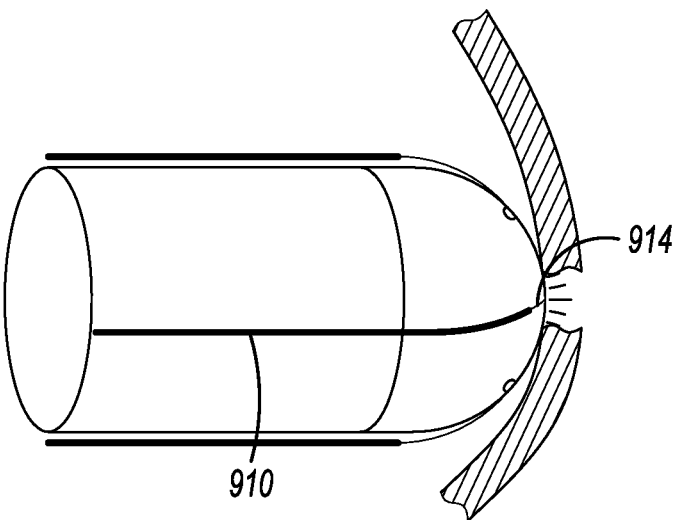
Figure 19C:
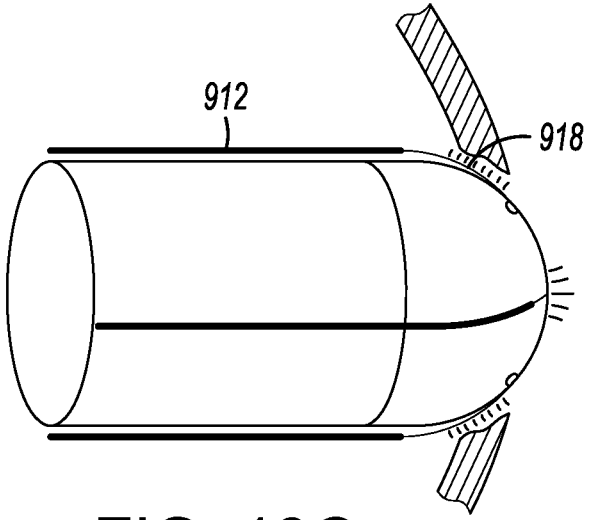
Figure 20A:
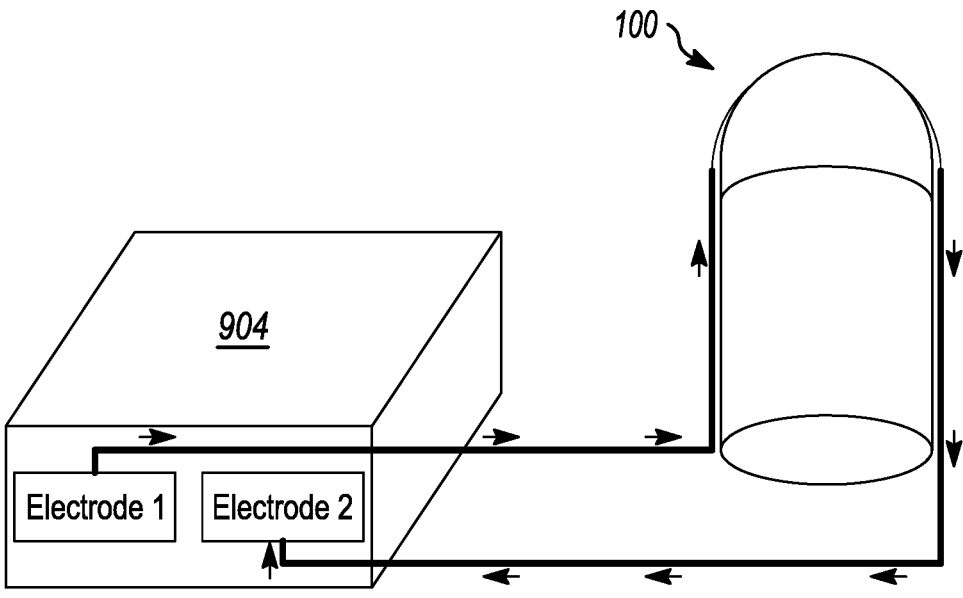
Figure 20B:
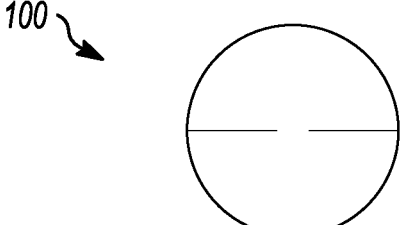

FIG. 18A and FIG. 18B depict a side view (FIG. 18A) and top view (FIG. 18B) of an embodiment of the elongated medical needle 100 of FIG. 1; and FIG. 19A to FIG. 19C depict a side views series of an embodiment of the elongated medical needle 100 of FIG. 1; and FIG. 20A and FIG. 20B depict a side view and top view, respectively, of an embodiment of the elongated medical needle 100 of FIG. 1 when connected to an energy source device.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS medical needle 100
elongated body 101
needle lumen 102
distal side portal 103
electrically-insulated distal section 104
   electrically-insulated proximal section 106
   electrically-conductive portion 108
   distal hole 109
   electrically-conductive wire 110
   internal conductor portion 112
   insulation portion 114
   channel 116
      guidewire assembly 800
      biological feature 900
patient 902
energy-source device 904
   first circuit emitting RF energy 910
second circuit emitting RF energy 912
   electrical cable 906
   first electrically conductive portion 914
   second electrically conductive portion 918
   insulated portion of first circuit 918
   insulated portion of second circuit 920

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

FIG. 1 to FIG. 9K depict side perspective views (FIG. 1, FIG. 3, FIG. 5 and FIG. 7) and top views (FIG. 2, FIG. 4, FIG. 6, FIG. 8 and FIG. 9A to 9K) of embodiments of an elongated medical needle 100.

Figure 9A:
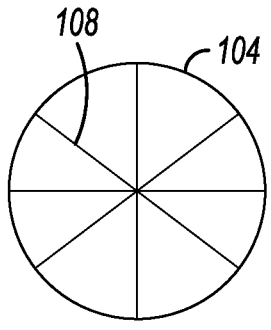
Figure 9B:
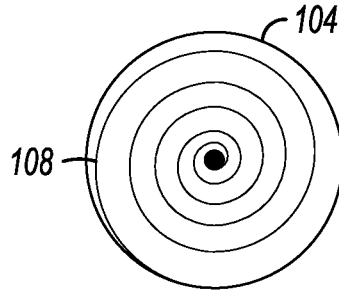
Figure 9C:
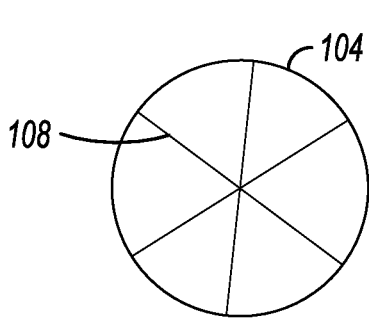
Figure 9D:
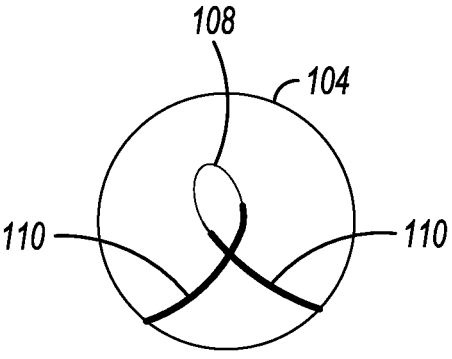
Figure 9E:
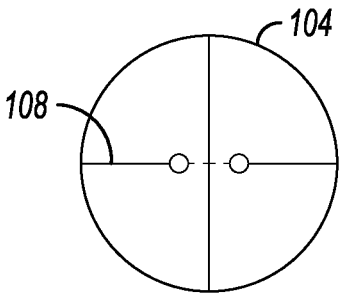
Figure 9F:
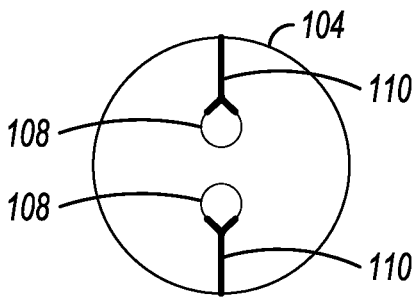
Figure 9G:
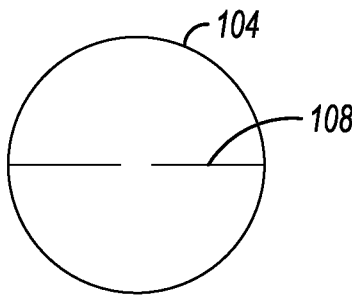
Figure 9H:
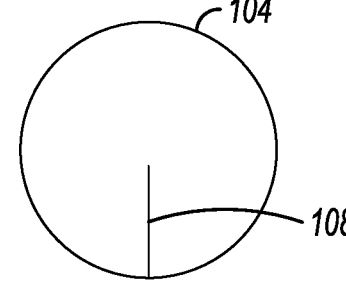
Figure 9I:
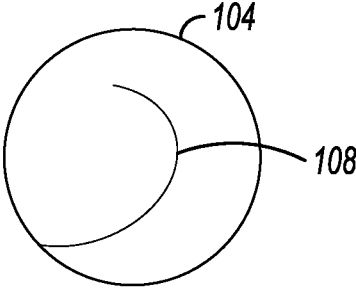
Figure 9J:
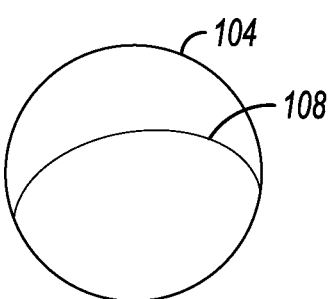
Figure 9K:
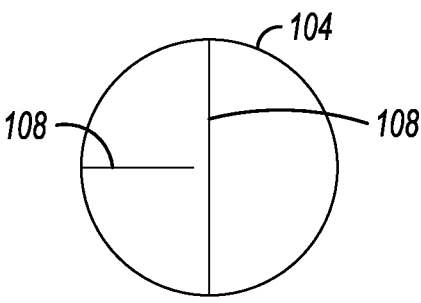
Figure 10:
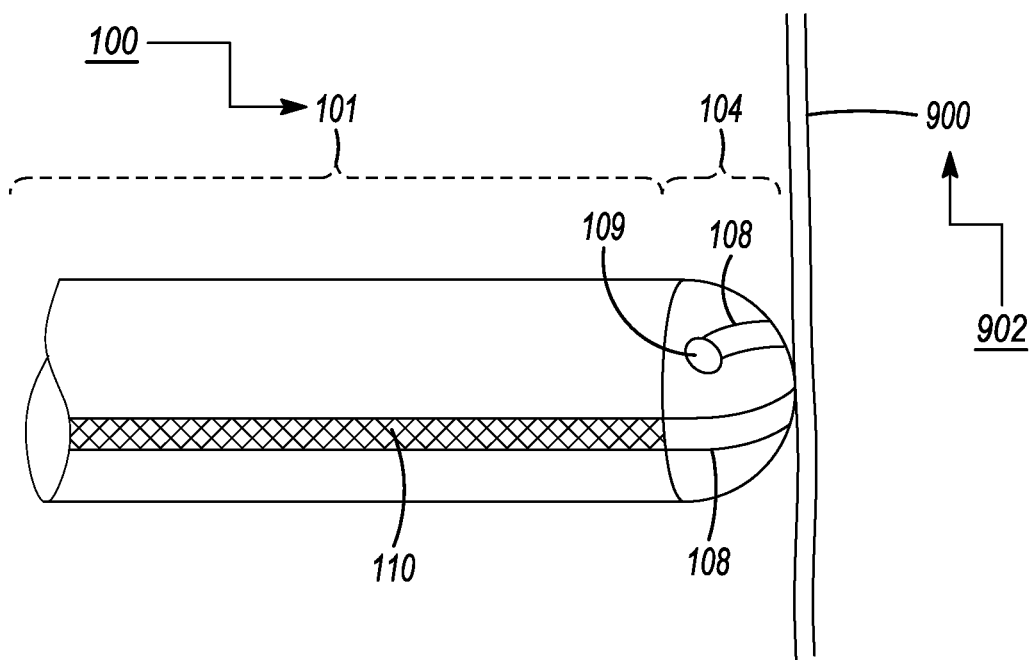
FIG. 10, FIG. 11 and FIG. 12 depict side perspective views of embodiments of the elongated medical needle of FIG. 3.
Figure 11:
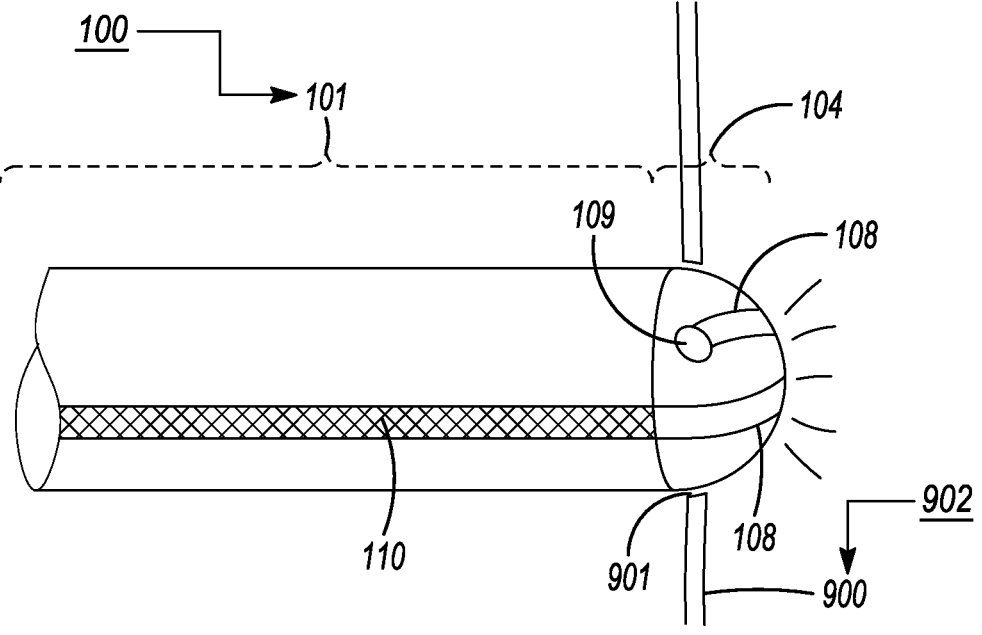
Figure 17:
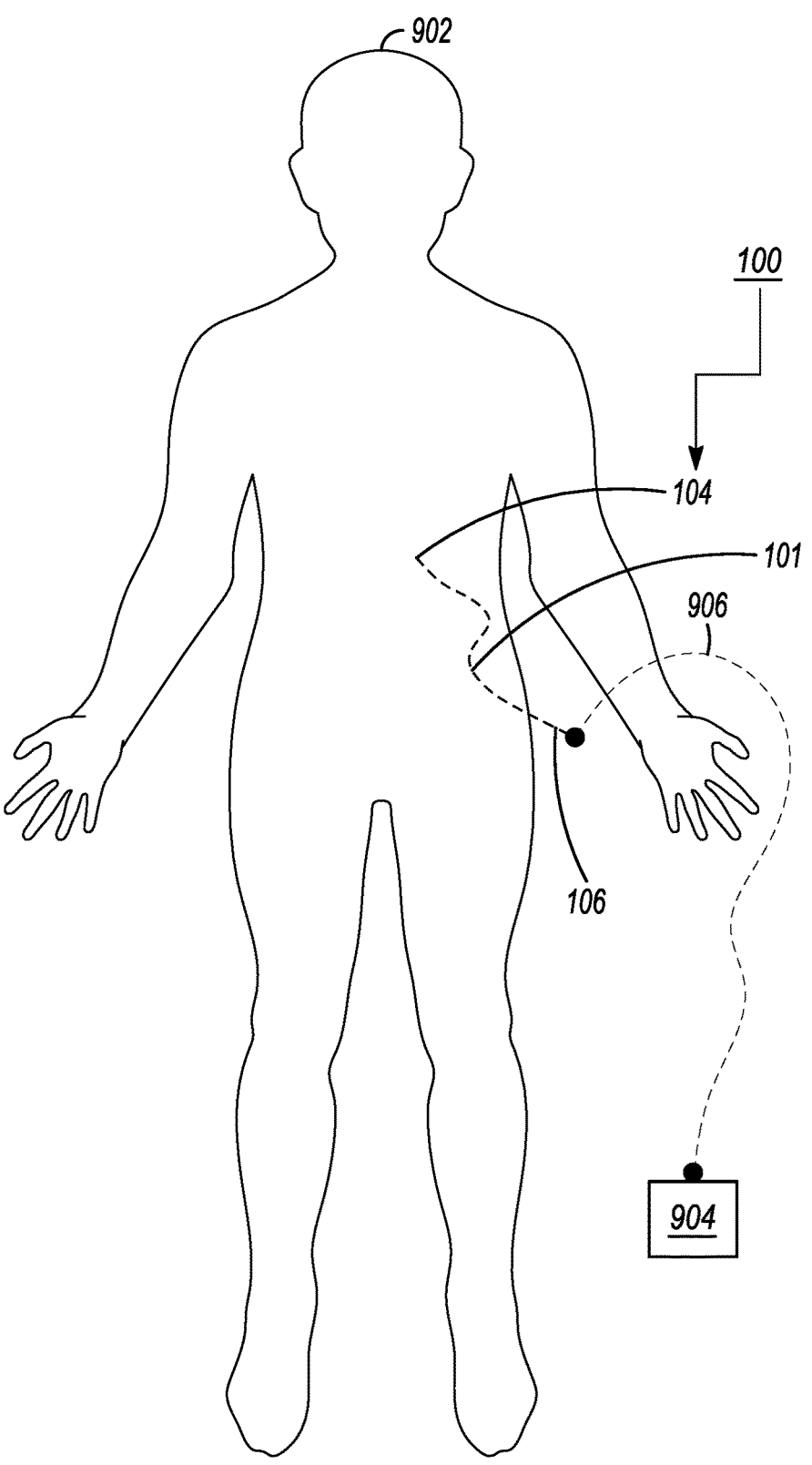

Referring to the embodiments (implementations) as depicted in FIG. 1, FIG. 3, FIG. 5 and FIG. 7, the elongated medical needle 100 is configured to be maneuvered toward, and positionable proximate to, the biological feature 900 of the patient 902 (as depicted in FIG. 10 and FIG. 11). The elongated medical needle 100 is configured to be inserted into a confined space defined by a living body (the patient). The elongated medical needle 100 includes (preferably) an electrically-insulated elongated body 101. The electrically-insulated elongated body 101 may be called a needle shaft. The electrically-insulated elongated body 101 has an outer surface extending between an electrically-insulated distal section 104 and an electrically-insulated proximal section 106 (the electrically-insulated proximal section 106 is depicted in FIG. 17). The electrically-insulated elongated body 101, the electrically-insulated distal section 104 and the electrically-insulated proximal section 106 are (each) electrically non-conductive (preferably in their entirety); that is, the electrically-insulated elongated body 101, the electrically-insulated distal section 104 and the electrically-insulated proximal section 106 are, preferably, entirely electrically non-conductive (they are, preferably, made entirely of an electrically non-conductive material). An alternative embodiment may include the electrically-insulated distal section 104 having a metallic outer layer (such as, a semi-spherical shell coated metallic layer formed on the exterior surface (of the electrically-insulated distal section 104) with an electrically insulative material (such as, polyimide and/or any equivalent thereof) formed on the metallic layer. As an alternative embodiment, the exterior surface of the metallic layer (such as the dome formed or positioned on the electrically-insulated distal section 104) may be masked during a polyimide coating process for the formation of a pattern of non-insulated portions of the metallic layer positioned (formed) on the electrically-insulated distal section 104; the formed pattern may include, for instance, a star-shaped pattern (which is a variation as depicted in FIG. 8), thereby increasing the number of lines from at least two (or more) lines (such as variations as depicted in FIG. 9A and FIG. 9C, both configuration extending across the outer tip of the electrically-insulated distal section 104), and/or may include a single circle or concentric circles, etc.

It will be appreciated that a variation of the embodiment as depicted in FIG. 4 may have vertically-extending lines as well thereby creating (forming) a grid pattern (if desired). It will be appreciated that the patterns may be created (formed) with wires or by masking the metallic layer (formed, for instance, as a metallic dome). An insulated electrically-conductive wire 110 is positioned proximately along the outer surface, and is aligned between the electrically-insulated distal section 104 and the electrically-insulated proximal section 106. For instance, the insulated electrically-conductive wire 110 may be positioned just above the outer surface (and is aligned between the electrically-insulated distal section 104 and the electrically-insulated proximal section 106). For instance, the insulated electrically-conductive wire 110 is, preferably, positioned below (just below) the outer surface (and is aligned between the electrically-insulated distal section 104 and the electrically-insulated proximal section 106). An exposed electrically-conductive portion 108 is mounted at the electrically-insulated distal section 104. The exposed electrically-conductive portion 108 is electrically connected to the insulated electrically-conductive wire 110. The electrically-conductive portion 108 is exposed, and may be arranged in any suitable configuration that facilitates tissue puncture.

Referring to the embodiments (implementations) as depicted in FIG. 1, FIG. 3, FIG. 5 and FIG. 7, the elongated medical needle 100 (and components thereof) include biocompatible material properties suitable for sufficient performance (such as, dielectric strength, thermal performance, electrical insulation, corrosion, water resistance, heat resistance, etc.) for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiments (implementations) as depicted in FIG. 1, FIG. 3, FIG. 5 and FIG. 7, the outer diameter of the insulated electrically-conductive wire 110 is, advantageously, smaller than (preferably, significantly smaller than) the outer diameter of the electrically-insulated elongated body 101. The amount of electrical insulation required for the electrically-conductive wire 110 is significantly less than the amount of electrical insulation required for the elongated body (which is entirely electrically conductive) associated with the known medical needle. The insulated electrically-conductive wire 110 utilizes significantly less electrical insulation which is in sharp contrast to the known medical needle having the elongated body that is (entirely) electrically conductive (the known medical needle, therefore, utilizes a substantially greater amount of electrical insulation, and this arrangement requires that the overall outer diameter of the known medical needle be significantly larger than the outer diameter of the electrically-insulated elongated body 101; therefore, the known medical needle is potentially limited in terms of possible medical applications). The elongated body of the known medical needle is made entirely of an electrically conductive material, and this is a significant, and disadvantageous, limiting factor (for the known medical needle). To summarize and emphasize: the insulated electrically-conductive wire 110 utilizes significantly less electrical insulation which is in sharp contrast to the known medical needle that is (entirely) electrically conductive; the known medical needle, therefore, utilizes substantially greater amount of electrical insulation and the overall outer diameter of the known medical needle, thereby potentially limits the application of the known medical needle. Therefore, the elongated medical needle 100, advantageously, may be deployed for a wider number of medical applications or uses.

Referring to the embodiments (implementations) as depicted in FIG. 1, FIG. 3, FIG. 5 and FIG. 7, the insulated electrically-conductive wire 110 (located at the electrically-insulated proximal section 106) is configured to be electrically connectable to an energy-source device 904 (the energy-source device 904 is depicted in FIG. 17). The energy-source device 904 is configured to generate energy, such as radiofrequency energy, etc., and any equivalent thereof. The exposed electrically-conductive portion 108 is configured to receive energy (such as radiofrequency energy, etc.) from the insulated electrically-conductive wire 110; this is done, preferably, in response to the insulated electrically-conductive wire 110 receiving the energy from an energy-source device 904 (the energy-source device 904 is depicted in FIG. 17). The exposed electrically-conductive portion 108 is configured to emit the energy, that was received from the insulated electrically-conductive wire 110 (from the energy-source device), toward the biological feature 900 (as depicted in FIG. 10 and FIG. 11); this is done, preferably after (A) the elongated medical needle 100 was maneuvered toward, and was positioned proximate to, the biological feature 900, and (B) the insulated electrically-conductive wire 110, in use, received energy from the energy-source device 904. The exposed electrically-conductive portion 108 is configured to puncture the biological feature 900 in response to selective emission of energy from the exposed electrically-conductive portion 108 toward the biological feature 900.

Referring to the embodiments (implementations) as depicted in FIG. 1, FIG. 3, FIG. 5 and FIG. 7, the medical needle 100 may be utilized in epicardial and/or transseptal access procedures, etc. For the case where the electrically-insulated elongated body 101 is deployed as an epicardial needle, the electrically-insulated elongated body 101 has an outer diameter of about 17 gauge and a length of about six (6) inches. For the case where the electrically-insulated elongated body 101 is deployed as an epicardial needle, any outer diameter can be used provided it does not create unnecessary trauma to patient anatomy. Any length can be used provided it is able to reach the desired patient anatomy. For the case where the electrically-insulated elongated body 101 is deployed as a transseptal needle, the electrically-insulated elongated body 101 has an outer diameter of about 0.030 inches to about 0.032 inches, and a length of about 67 to about 91 centimeters. For the case where the electrically-insulated elongated body 101 is deployed as a transseptal needle, any outer diameter can be used provided it can still fit in the patient's anatomy. Any length can be used provided it is able to reach the desired patient anatomy from the chosen access site.

Referring to the embodiment (implementation) as depicted in FIG. 1, the electrically-insulated distal section 104 includes (or entirely includes), preferably, a non-conductive cap made of a heatshrink material, preferably the polytetrafluoroethylene (PTFE) heat shrink material or hybrid polyurethane. Preferably, there is no layer of electrical insulation positioned over the electrically-insulated distal section 104. The electrically-insulated distal section 104 may be called a needle distal tip. The electrically-insulated distal section 104 may have any configuration and/or material for the electrical insulation purposes (that is, the electrically-insulated distal section 104 is entirely electrically non-conductive).

Referring to the embodiment (implementation) as depicted in FIG. 1, the insulated electrically-conductive wire 110 may have a core material of stainless steel or nitinol. The insulated electrically-conductive wire 110 may have an outer layer of electrical insulation of PTFE heat shrink. Alternatively, the insulated electrically-conductive wire 110 may have an outer layer of electrical insulation of hybrid polyurethane. The insulated electrically-conductive wire 110 may be aligned (runs) along the exterior of the elongated body 101, and into the electrical cable 906 (as depicted in FIG. 17) proximally. The insulated electrically-conductive wire 110 may include any conductive element. The electrically-insulated elongated body 101 can be any biocompatible material provided it has sufficient stiffness to traverse the necessary anatomy and/or vasculature of the patient.

Referring to the embodiments (implementations) as depicted in FIG. 1 and FIG. 2, the electrically-conductive portion 108 forms a square-shaped profile (a rectilinear profile) positioned over the electrically-insulated distal section 104.

Referring to the embodiments (implementations) as depicted in FIG. 3 and FIG. 4, the electrically-conductive portion 108 forms a grouping of parallel lines extending across the outer tip of the electrically-insulated distal section 104. The parallel lines may act to score the tissue of a biological wall, enabling easier penetration with the elongated medical needle 100.

Referring to the embodiments (implementations) as depicted in FIG. 5 and FIG. 6, the electrically-conductive portion 108 forms a line (preferably, a single line) extending across the outer tip of the electrically-insulated distal section 104.

Referring to the embodiments (implementations) as depicted in FIG. 7 and FIG. 8, the electrically-conductive portion 108 forms an X-shaped configuration extending across the outer tip of the electrically-insulated distal section 104.

Further examples of variation or embodiment of FIG. 2, FIG. 4, FIG. 6 or FIG. 8 may include configuration of: (1) FIG. 9B (where the electrically-conductive portion 108 forms a spiral-shaped configuration extending across the outer tip of the electrically-insulated distal section 104); (2) FIG. 9D (where electrically conductive portion 108 forms a partial loop extending across the outer tip of the electrically-insulated distal section 104, in which a section of the loop is electrically insulated in order to avoid creating an electrically-conductive closed-loop portion); (3) FIG. 9E (which may be used/implemented in a monopolar, bipolar, or multiple circuit configuration); (4) FIG. 9F (where partial electrically-conductive loops are formed at each end of the electrically-insulated distal section 104, which may be used/implemented in a bipolar, or multiple circuit configuration); (5) FIG. 9G (where the electrically-conductive portions 108 form lines along the electrically-insulated distal section 104, which may be used/implemented in a bipolar, or multiple circuit configuration); (6) FIG. 9H (where the electrically-conductive portion 108 forms a partial line along a portion of the electrically-insulated distal section 104); (7) FIG. 9I (where the electrically-conductive portion 108 forms a spline along a portion of the electrically-insulated distal section 104); (8) FIG. 9J (where the electrically-conductive portion 108 forms a spline along the entire length of the electrically-insulated section 104); and (9) FIG. 9K, where the electrically-conductive portion 108 of one electrode or circuit forms a partial line along a portion of the electrically-insulated distal section 104, while the electrically-conductive portion of a second electrode or circuit forms a complete line along the electrically-insulated distal section 104. The embodiment of FIG. 9K could be implemented in a bipolar or multiple circuit configuration.

Figure 12:
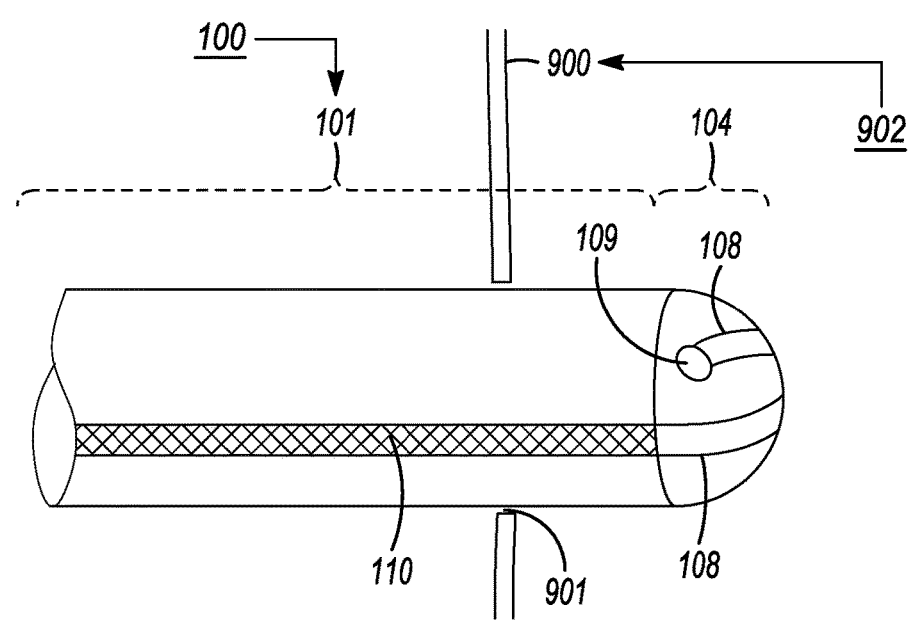

FIG. 10, FIG. 11 and FIG. 12 depict side perspective views of embodiments of the elongated medical needle 100 of FIG. 3.

Referring to the embodiments (implementations) as depicted in FIG. 10, FIG. 11 and FIG. 12, a method is depicted for emitting energy toward the biological feature 900 of the patient 902. The method includes (as depicted in FIG. 10) maneuvering and positioning an elongated medical needle 100 toward, and proximate to, the biological feature 900 of the patient 902. The method also includes (as depicted in FIG. 11) sending the energy to the exposed electrically-conductive portion 108, in use, along the insulated electrically-conductive wire 110 in response to the insulated electrically-conductive wire 110 receiving the energy from the energy-source device 904 (as depicted in FIG. 17). The method also includes (as depicted in FIG. 11) emitting the energy from the exposed electrically-conductive portion 108, in use, toward the biological feature 900, in which the energy was received from the insulated electrically-conductive wire 110, after the elongated medical needle 100 was maneuvered toward, and was positioned proximate to, the biological feature 900, and after the insulated electrically-conductive wire 110, in use, received energy from the energy-source device 904. Once the biological feature 900 was punctured, the energy-source device 904 is deactivated, and the elongated medical needle 100 may be advanced forwardly (if so desired); for instance, the elongated medical needle 100 may traverse the biological feature 900 (tissue wall). The biological feature 900 may include, for instance, the pericardium layer of the heart or the interatrial septum, etc. It will be appreciated that FIG. 10 and FIG. 11 are specifically related to (associated with) FIG. 3 or FIG. 7, and that the method is applicable for all embodiments of the elongated medical needle 100.

Figure 13:
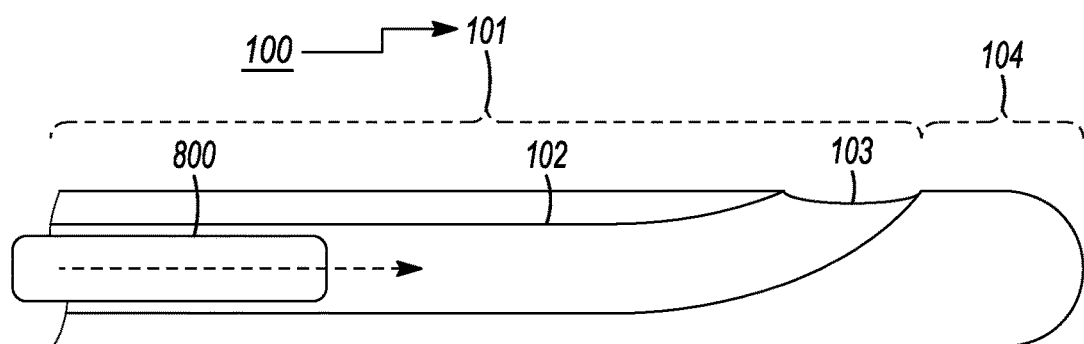
FIG. 13 and FIG. 14 depict side perspective views of embodiments of the elongated medical needle of FIG. 1.
Figure 14:
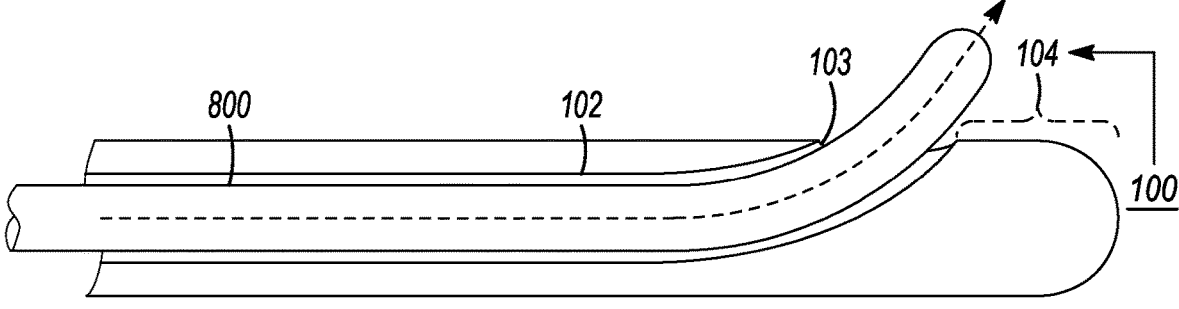

FIG. 13 and FIG. 14 depict side perspective views of embodiments of the elongated medical needle 100 of FIG. 1.

Referring to the embodiments (implementations) as depicted in FIG. 13 and FIG. 14, the electrically-insulated elongated body 101 defines (in accordance with an optional embodiment) an elongated needle lumen 102. The elongated needle lumen 102 extends between the electrically-insulated distal section 104 and the electrically-insulated proximal section 106 (the electrically-insulated proximal section 106 is depicted in FIG. 17). Advantageously, an interior of the elongated needle lumen 102 is electrically insulated by the electrically-insulated elongated body 101, and therefore the patient is protected from electrical hazards from any sort of device that might be inserted into the elongated needle lumen 102. The elongated needle lumen 102 may accept an electrically-conductive element or a device (such as, an elongated guidewire assembly 800). The elongated needle lumen 102 is configured to slidably receive, at least in part, the elongated guidewire assembly 800, and to guide movement of the guidewire assembly 800 between the electrically-insulated proximal section 106 and the electrically-insulated distal section 104.

Referring to the embodiments (implementations) as depicted in FIG. 13 and FIG. 14, the elongated needle lumen 102 may provide a sloped surface leading to a distal side portal 103 formed through the outer surface of the side wall of the elongated needle lumen 102. Advantageously, this arrangement may facilitate fluid flow and guidewire insertion through the elongated needle lumen 102 (if required). The distal side portal 103 may be called a needle distal side port.

Figure 15:
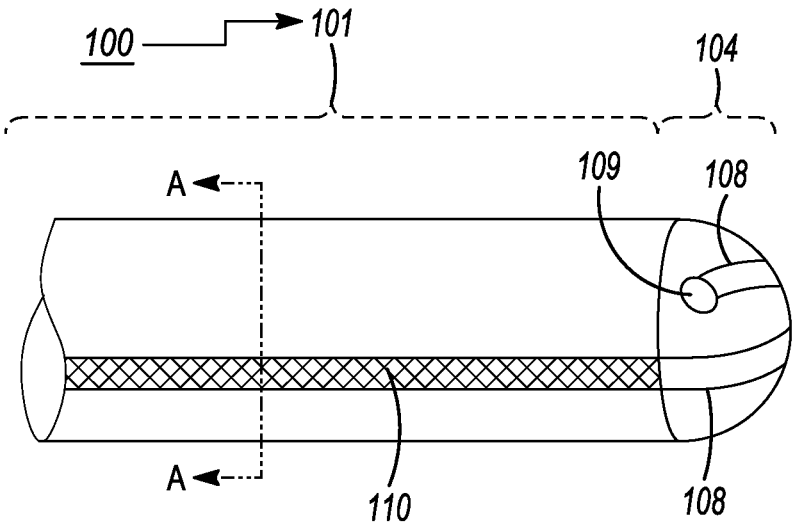
FIG. 15, FIG. 16 and FIG. 17 depict a side perspective view (FIG. 15), a cross-sectional view (FIG. 16) and a schematic view (FIG. 17) of embodiments of the elongated medical needle of FIG. 1.
Figure 16:
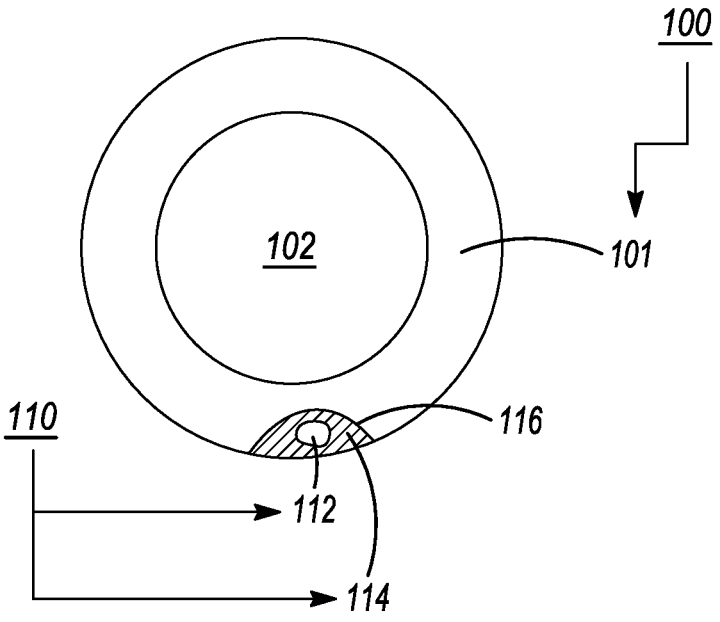

FIG. 15, FIG. 16 and FIG. 17 depict a side perspective view (FIG. 15), a cross-sectional view (FIG. 16) and a schematic view (FIG. 17) of embodiments of the elongated medical needle 100 of FIG. 1. The cross-sectional view of FIG. 16 is taken through a cross-sectional line A-A of FIG. 15.

Referring to the embodiments (implementations) as depicted in FIG. 15 and/or FIG. 16, it will be appreciated that FIG. 15 is related to (associated with) FIG. 3 and FIG. 7. A channel 116 (at least one or more channels, and the channel 116 is depicted in FIG. 16 with more clarity) may be formed in (cut into) the electrically-insulated distal section 104 (and/or the electrically-insulated elongated body 101) for the purpose of receiving (at least in part) the electrically-conductive wire 110. In this manner, the outer surface of the electrically-insulated distal section 104 (and/or the electrically-insulated elongated body 101) may be entirely smooth. The channel 116, as depicted in FIG. 16, is formed on the outer surface of the electrically-insulated elongated body 101. The insulated electrically-conductive wire 110 includes an internal conductor portion 112 (depicted in FIG. 16) surrounded by an insulation portion 114. The insulation portion 114 is received within the channel 116.

Referring to the embodiment (implementation) as depicted in FIG. 17, it will be appreciated that a hub section (known and not depicted) may be provided, and is configured to provide a user-grip section for the user (at the proximal end of the medical needle 100). The hub section may provide a compatible port for syringes to facilitate fluid injection. The electrical cable 906 facilitates connection of the electrically-conductive portion 108 to the energy-source device 904 (such as the radiofrequency generator, etc.). The electrical cable 906 may include any cable that facilitates a connection to the energy-source device 904 (such as a radiofrequency generator). For instance, the energy-source device 904 may include the source device associated with the BAYLIS (TRADEMARK) POWERWIRE (REGISTERED TRADEMARK) radio frequency guidewire manufactured by BAYLIS MEDICAL COMPANY (headquartered in Canada).

FIG. 18A and FIG. 18B depict a side view (FIG. 18A) and top view (FIG. 18B) of an embodiment of the elongated medical needle 100 of FIG. 1. FIG. 19A to FIG. 19C depict a side views series of an embodiment of the elongated medical needle 100 of FIG. 1. FIG. 20A and FIG. 20B depict a side view and top view, respectively, of an embodiment of the elongated medical needle 100 of FIG. 1 when connected to an energy source device.

Referring to the embodiments as depicted in FIG. 18A and FIG. 18B, the elongated medical needle 100 may have two circuits (910 and 912) emitting RF energy. A first circuit 910 is configured to deliver RF energy at the first electrically-conductive portion 914 while a second circuit 912 is configured to be differentially selected to deliver RF energy at the second electrically-conductive portion 918 in order to achieve more cutting for challenging or thicker biological walls 900. One of the circuits may be diverted through a distal hole 109 in order to avoid contact with the electrically-conductive portion of the other circuit. Alternatively, the electrically-conductive portion 914 of the first circuit 910 may simply terminate before coming into contact with the electrically-conductive portion 918 of the second circuit 912. The electrically conductive portions of each circuit may be fixed to the electrically insulated distal section 104 via glue. Alternatively, the electrically conductive portions may be left un-fixed to the electrically insulated distal section 104 while the insulated portions of the electrically conductive wires 110 are fixed to the elongated body 101 via glue or direct molding onto the elongated body 101.

Referring to the embodiments as depicted in FIG. 19A to FIG. 19C, the elongated medical needle 100 with two circuits 910 and 912 is shown traversing through a tissue wall 900. In FIG. 19A, the circuits are inactive and the elongated medical needle 100 is shown applying a tenting force to the biological wall 900. In FIG. 19B, the first circuit 910 is active and the electrically-conductive portion 914 is shown to be cutting the biological wall 900. In FIG. 19C, the electrically-conductive portion 918 of the second circuit 912 is activated in order to facilitate more cutting of the biological wall 900.

Referring to the embodiments as depicted in FIG. 20A, an optional bipolar configuration is shown on the elongated medical needle 100. Electron flow is from the first electrode on the generator (energy source device) 904 to the second electrode (shown by an arrow in GIG. 20A), eliminating the need for a dispersive ground electrode that is required with monopolar electrode configurations. Electrically-conductive portions form first electrode (electrode 1) and second electrode (electrode 2) on the elongated medical needle 100.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for use with a biological feature of a patient, the apparatus comprising:

an elongated medical needle configured to be maneuvered toward, and positionable proximate to, the biological feature of the patient, the elongated medical needle including an electrically-insulated elongated body having an outer surface extending between an electrically-insulated distal section and an electrically-insulated proximal section;

an insulated electrically-conductive wire aligned along the outer surface of the electrically-insulated elongated body and positioned external to the electrically-insulated elongated body, the insulated electrically-conductive wire extending between the electrically-insulated distal section and the electrically-insulated proximal section, the insulated electrically-conductive wire being configured to be electrically connectable to an energy-source device; and an exposed electrically-conductive portion located at the electrically-insulated distal section, the exposed electrically-conductive portion being electrically connected to the insulated electrically-conductive wire, the exposed electrically-conductive portion being configured to receive energy from the insulated electrically-conductive wire in response to the insulated electrically-conductive wire receiving the energy from the energy-source device, and the exposed electrically-conductive portion further being configured to emit the energy, that was received from the insulated electrically-conductive wire, toward the biological feature after the elongated medical needle was maneuvered toward, and was positioned proximate to, the biological feature.

2. The apparatus of claim 1, wherein the electrically-insulated elongated body defines an elongated needle lumen extending between the electrically-insulated distal section and the electrically-insulated proximal section, wherein the elongated needle lumen is configured to slidably receive, at least in part, an elongated guidewire assembly, and to guide movement of the elongated guidewire assembly between the electrically-insulated proximal section and the electrically-insulated distal section, and wherein an interior of the elongated needle lumen is electrically insulated by the electrically-insulated elongated body.

3. The apparatus of claim 2, wherein the elongated needle lumen provides a sloped surface leading to a distal side portal formed through the outer surface of a side wall of the elongated needle lumen.

4. The apparatus of claim 1, wherein the exposed electrically-conductive portion is also configured to puncture the biological feature in response to selective emission of energy from the exposed electrically-conductive portion, in use, toward the biological feature.

5. The apparatus of claim 1, wherein an outer diameter of the insulated electrically-conductive wire is smaller than an outer diameter of the electrically-insulated elongated body.

6. The apparatus of claim 1, wherein the electrically-insulated distal section includes a non-conductive cap.

7. The apparatus of claim 1, wherein the exposed electrically-conductive portion forms a grouping of parallel lines extending across an outer tip of the electrically-insulated distal section.

8. The apparatus of claim 1, wherein the exposed electrically-conductive portion forms one or more lines extending across an outer tip of the electrically-insulated distal section.

9. The apparatus of claim 1, wherein the exposed electrically-conductive portion forms an X-shaped configuration extending across an outer tip of the electrically-insulated distal section.

10. The apparatus of claim 1, wherein a channel is formed on the electrically-insulated elongated body and the electrically-insulated distal section for receiving, at least in part, the insulated electrically-conductive wire.

11. The apparatus of claim 10, wherein the insulated electrically-conductive wire includes an internal conductor portion surrounded by an insulation portion, and the insulation portion is received within the channel.

12. The apparatus of claim 1, wherein the electrically-insulated distal section has a metallic outer layer formed on an exterior surface of the electrically-insulated distal section, and an electrically insulative material is formed on the metallic outer layer.

13. The apparatus of claim 1, wherein the electrically-insulated distal section has a metallic outer layer forming a pattern of non-insulated portions.

14. The apparatus of claim 1, wherein the elongated medical needle has a first circuit and a second circuit for emitting radio frequency (RF) energy.

15. The apparatus of claim 14, wherein the first circuit is configured to deliver RF energy at a first electrically-conductive portion while the second circuit is configured to be differentially selected to deliver RF energy at a second electrically-conductive portion.

16. The apparatus of claim 15, wherein partial electrically-conductive loops are formed at two ends of the electrically insulated distal section.

17. The apparatus of claim 1, wherein the exposed electrically-conductive portion has a first and second electrode or circuit, said first electrode or circuit forms a partial line along a portion of the electrically-insulated distal section while the exposed electrically-conductive portion of said second electrode or circuit forms a complete line along the electrically-insulated distal section.

18. An apparatus for use with a biological feature of a patient, the apparatus comprising:
  an elongated medical needle configured to be maneuvered toward, and positionable proximate to, the biological feature of the patient, the elongated medical needle including an electrically-insulated elongated body having an outer surface extending between an electrically-insulated distal section and an electrically-insulated proximal section;
  an insulated electrically-conductive wire aligned along the outer surface of the electrically-insulated elongated body, the insulated electrically-conductive wire extending between the electrically-insulated distal section and the electrically-insulated proximal section, the insulated electrically-conductive wire being configured to be electrically connectable to an energy-source device; and
  an exposed electrically-conductive portion located at the electrically-insulated distal section, the exposed electrically-conductive portion being electrically connected to the insulated electrically-conductive wire, the exposed electrically-conductive portion being configured to receive energy from the insulated electrically-conductive wire in response to the insulated electrically-conductive wire receiving the energy from the energy-source device, and the exposed electrically-conductive portion further being configured to emit the energy, that was received from the insulated electrically-conductive wire, toward the biological feature after the elongated medical needle was maneuvered toward, and was positioned proximate to, the biological feature, wherein the exposed electrically-conductive portion forms a rectilinear profile positioned over the electrically-insulated distal section.

19. An apparatus for use with a biological feature of a patient, the apparatus comprising:
  an elongated medical needle configured to be maneuvered toward, and positionable proximate to, the biological feature of the patient, the elongated medical needle including an electrically-insulated elongated body having an outer surface extending between an electrically-insulated distal section and an electrically-insulated proximal section;
  an insulated electrically-conductive wire being aligned along the outer surface of the electrically-insulated elongated body between the electrically-insulated distal section and the electrically-insulated proximal section, wherein the insulated electrically-conductive wire is positioned external to the electrically-insulated elongated body; and
  an exposed electrically-conductive portion mounted at the electrically-insulated distal section, the exposed electrically-conductive portion being electrically connected to the insulated electrically-conductive wire.

20. The apparatus of claim 19, wherein the exposed electrically-conductive portion forms a rectilinear profile positioned over the electrically-insulated distal section.

\* \* \* \* \*